(12) United States Patent
Ecker et al.

(10) Patent No.: US 8,536,401 B2
(45) Date of Patent: Sep. 17, 2013

(54) FEMININE HYGIENE ARTICLE WITH PRINTED PATTERN AND EMBOSSED PATTERN

(75) Inventors: Cornelia Ecker, Schwalbach (DE); Ivano Gagliardi, Pescara (IT); Paolo Veglio, Pescara (IT)

(73) Assignee: The Procter and Gamble Company, Cincinnati, OH (US)

( * ) Notice: Subject to any disclaimer, the term of this patent is extended or adjusted under 35 U.S.C. 154(b) by 216 days.

(21) Appl. No.: 12/123,705

(22) Filed: May 20, 2008

(65) Prior Publication Data

US 2008/0294140 A1 Nov. 27, 2008

(30) Foreign Application Priority Data

May 25, 2007 (EP) .................................. 07108949

(51) Int. Cl.
*A61F 13/15* (2006.01)
*A61F 13/20* (2006.01)

(52) U.S. Cl.
USPC ..................................... 604/380; 604/385.01

(58) Field of Classification Search
USPC .......... 604/367, 380, 385.01, 385.03, 385.23, 604/387
See application file for complete search history.

(56) References Cited

U.S. PATENT DOCUMENTS

| 4,518,451 A | 5/1985 | Luceri et al. |
| 4,623,340 A | 11/1986 | Luceri |
| 5,795,345 A * | 8/1998 | Mizutani et al. ............. 604/380 |
| 5,897,541 A | 4/1999 | Uitenbroek et al. |
| 6,780,270 B2 * | 8/2004 | Andersson .................... 156/209 |
| 7,686,790 B2 | 3/2010 | Rasmussen et al. |
| 7,824,385 B2 | 11/2010 | Ecker et al. |
| 2003/0026945 A1 * | 2/2003 | Lasko .......................... 428/131 |
| 2004/0015145 A1 | 1/2004 | Miura et al. |
| 2004/0265544 A1 | 12/2004 | Di Salvo et al. |
| 2005/0154365 A1 * | 7/2005 | Zander et al. ............ 604/385.04 |
| 2005/0192549 A1 * | 9/2005 | Veglio et al. .................. 604/367 |
| 2006/0111684 A1 * | 5/2006 | Berba et al. .................... 604/361 |
| 2006/0129116 A1 * | 6/2006 | Hughes et al. ................ 604/361 |
| 2006/0135927 A1 | 6/2006 | Zander et al. |
| 2006/0142710 A1 * | 6/2006 | Kigata et al. .................. 604/361 |

FOREIGN PATENT DOCUMENTS

| JP | 2005/312694 | 11/2005 |
| WO | WO 2004/006818 A1 | 1/2004 |
| WO | WO 2004057110 A1 * | 7/2004 |
| WO | WO 2005084597 A1 * | 9/2005 |
| WO | WO 2006/050095 | 5/2006 |
| WO | WO 2006/068673 | 6/2006 |

OTHER PUBLICATIONS

PCT International Search Report dated Oct. 15, 2008.
European Search Report dated Aug. 10, 2010.

* cited by examiner

*Primary Examiner* — Michele M Kidwell
(74) *Attorney, Agent, or Firm* — Andrew J. Hagerty; Megan C. Hymore; Amanda T. Barry

(57) ABSTRACT

A feminine hygiene article such as pantiliner having a topsheet and a backsheet. The article further includes a printed pattern and an embossed pattern. The embossed pattern has at least one embossed decorative element and the printed pattern has a printed decorative element which is substantially similar to the embossed decorative element.

12 Claims, 8 Drawing Sheets

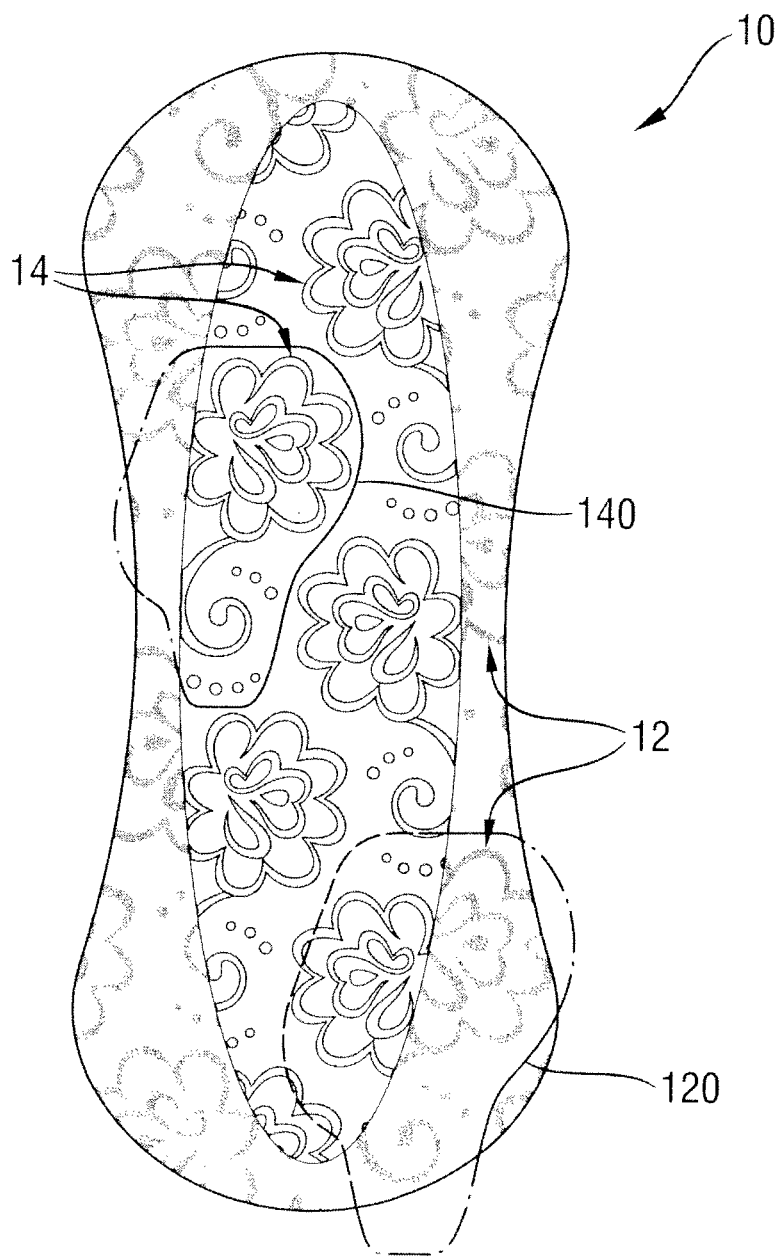

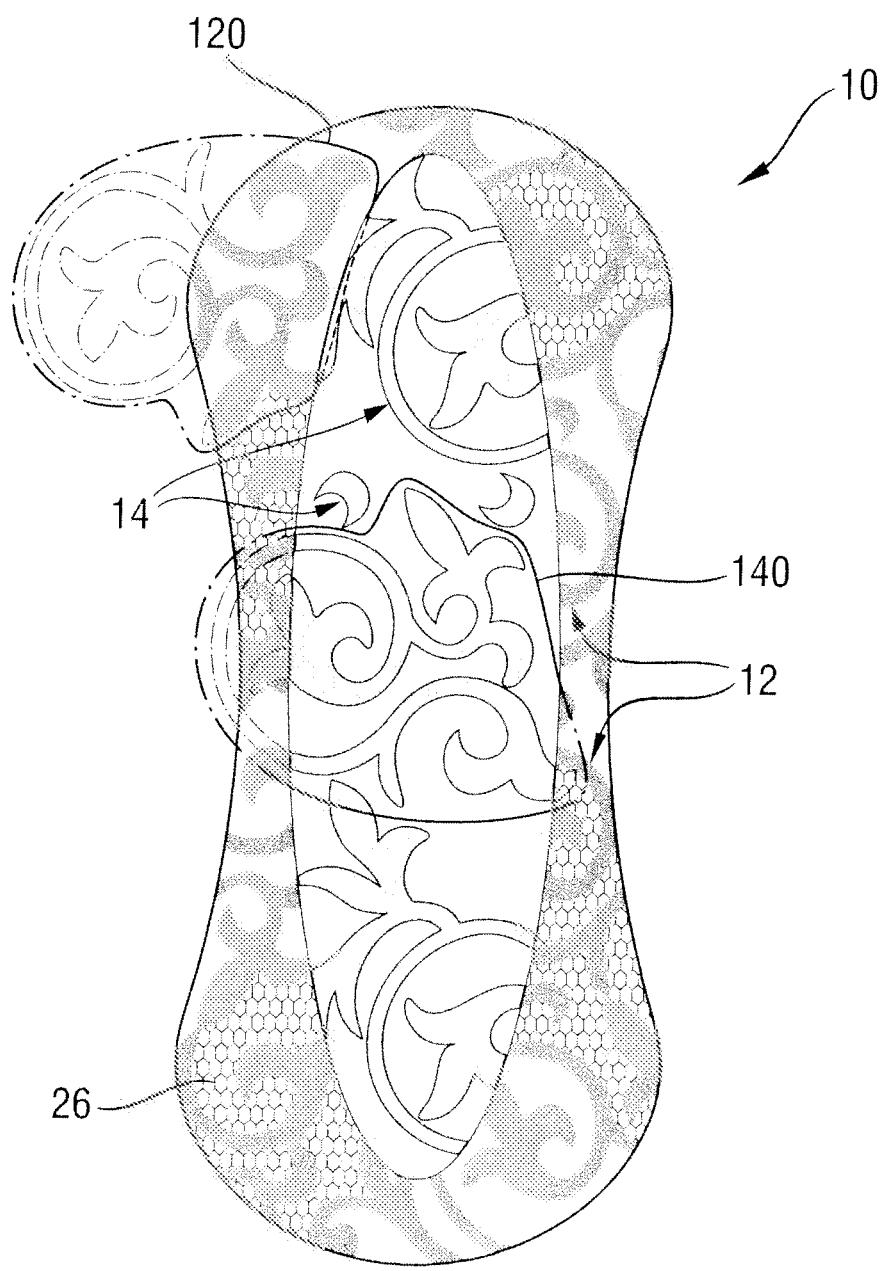

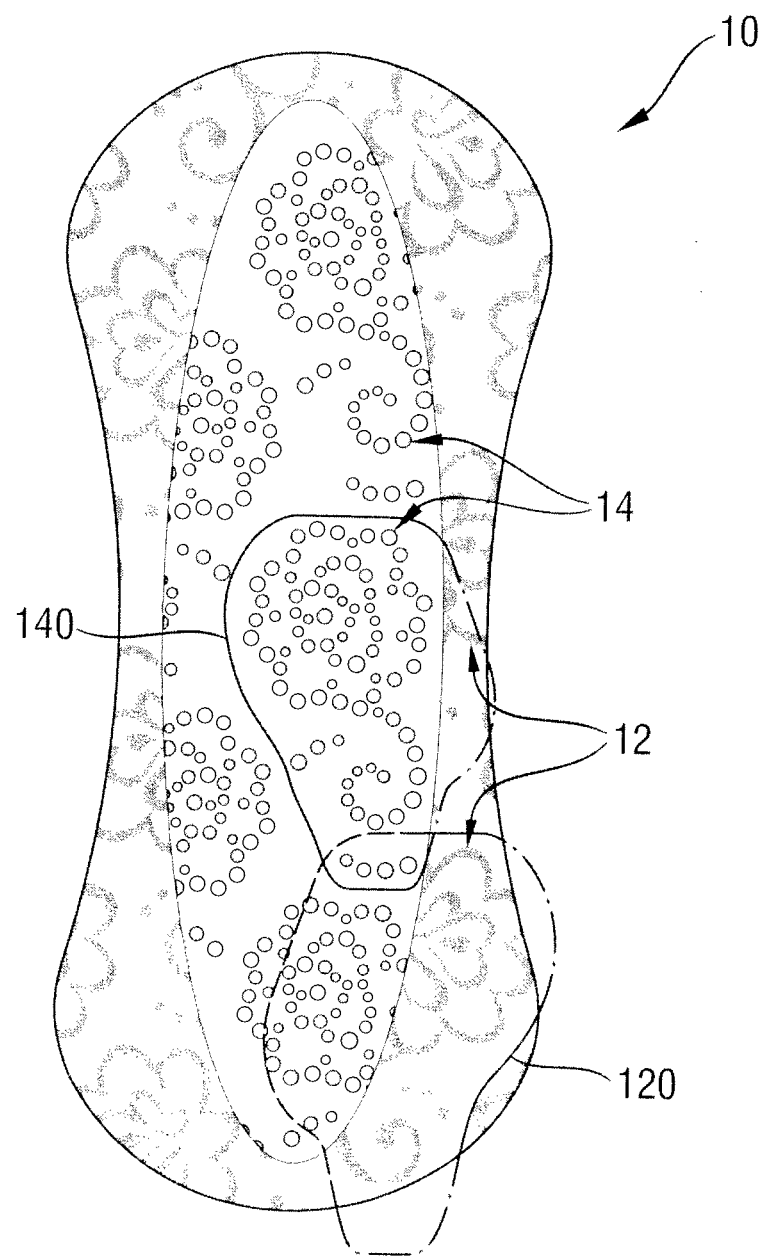

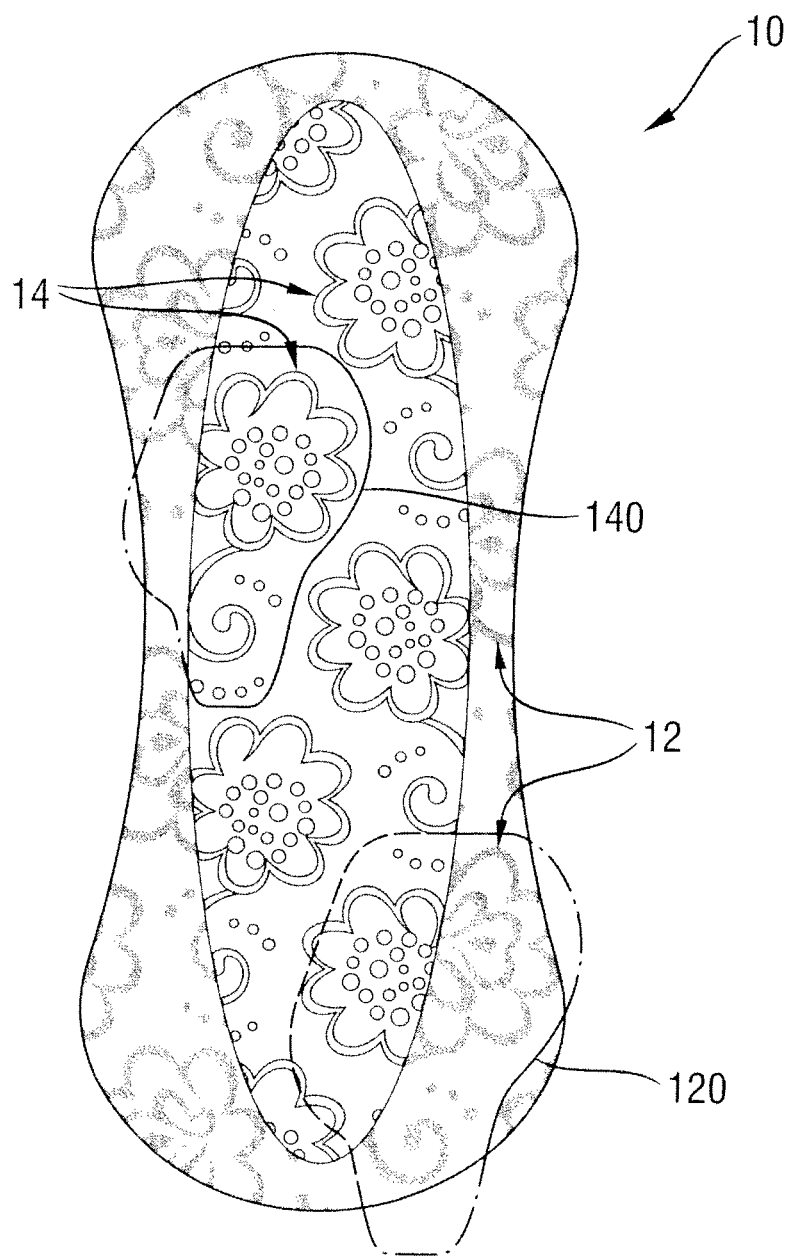

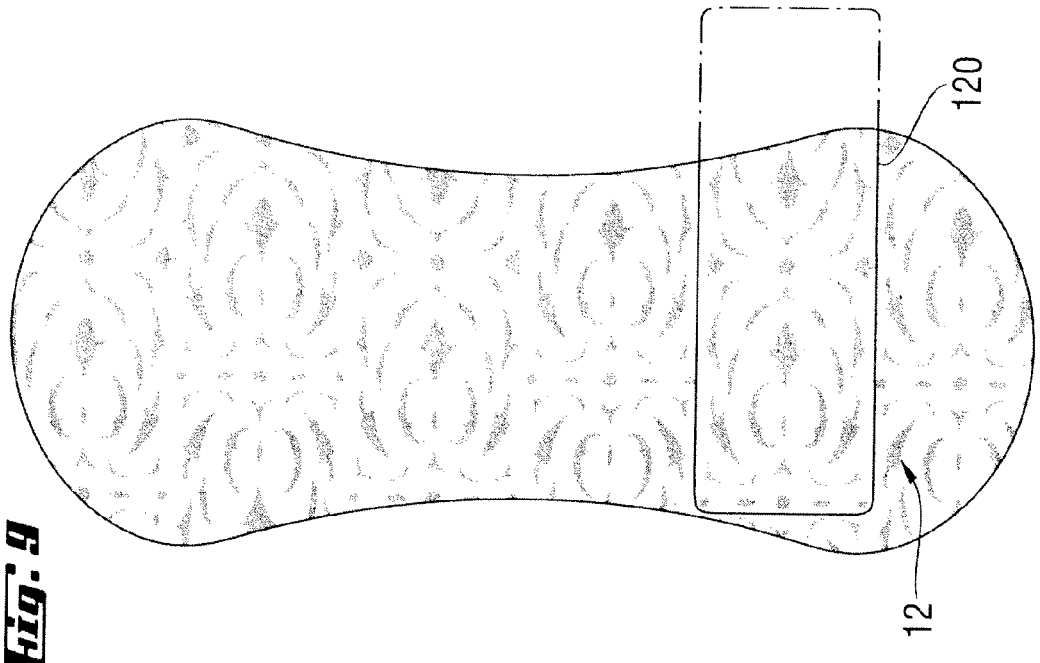
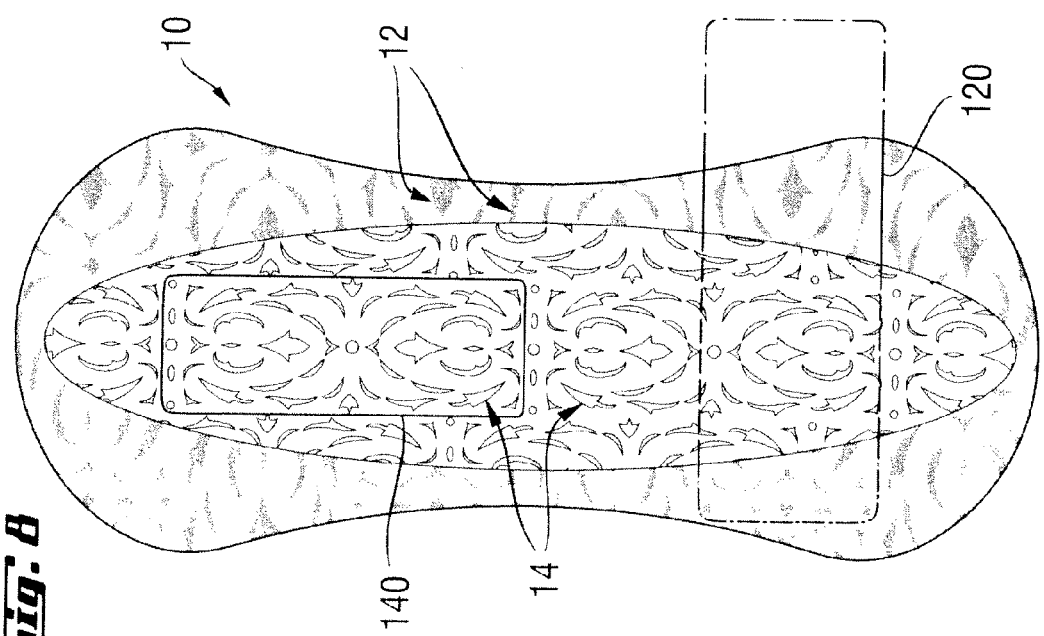

FEMININE HYGIENE ARTICLE WITH PRINTED PATTERN AND EMBOSSED PATTERN

FIELD OF THE INVENTION

The present invention relates to absorbent articles for feminine personal hygiene such as pantiliners or sanitary napkins. The articles of the invention comprise a printed pattern and an embossed pattern.

BACKGROUND OF THE INVENTION

Feminine hygiene articles such as sanitary napkins (also called pads) may be used by women during their menstrual periods to receive and contain menses and other bodily discharges. Feminine hygiene articles often called pantiliners may also be used by women with lower physical needs or outside the menstrual period for general hygiene and cleanliness. Other feminine hygiene articles, such as incontinence pads are similarly worn between the uro-genital area of the user and their underwear for control of light urine incontinence.

It is common for the body-facing side of feminine hygiene articles (i.e. the topsheet) to be embossed. For example, embossed channels can bring benefits in terms of improved fluid penetration, prevention of side leakages and/or improved conformability of the product. Embossing may also be used to bond different layers together and/or provide an improved appearance to the body-facing side of the article.

Feminine hygiene articles are sometimes provided with a printed pattern on one of the layer of the articles. However, there is a consumer prejudice against the presence of dye or ink in direct contact with the skin, i.e. on the topsheet side of the article. Hence, few feminine hygiene products comprise a decorative printed pattern.

WO2004/006818A1 discloses an absorbent article having a graphic visible through the body contacting surface, wherein the graphic is printed on the body facing surface of the backsheet or the garment facing side of the topsheet. The topsheet and absorbent core can be provided with embossed channels.

There is an unsolved problem of providing a feminine hygiene article with an improved overall appearance. In particular, there is a need for an article providing an improved overall appearance without the negative of having a dye or ink printed on the topsheet of the article.

SUMMARY OF THE INVENTION

The present invention is for a feminine hygiene article comprising a topsheet and a backsheet. The article further comprises a printed pattern and an embossed pattern. The embossed pattern comprises at least one embossed decorative element. In a first aspect of the invention, the printed pattern comprises a printed decorative element which is substantially similar to the embossed decorative element. In a second aspect of the present invention, an absorbent core is present between the topsheet and backsheet and the printed pattern is printed on a layer of the article situated below the absorbent core, such as the backsheet. In the second aspect, the printed pattern is visible through at least a portion of the topsheet outside the core area of the topsheet (the area overlying the core), and the embossed pattern is at least partially embossed within the core area.

More specifically, the article is a feminine hygiene article, such as a pantiliner, including a topsheet, a backsheet joined to the topsheet, a printed pattern including at least one printed decorative element and an embossed pattern including at least one embossed decorative element, the printed decorative element and the embossed decorative element being substantially similar. The absorbent article includes an absorbent core between the topsheet and the backsheet, with the printed layer printed on a layer of the article situated below the absorbent core, and at least a portion of the printed pattern being visible through the topsheet. In at least one embodiment, the printed pattern is not visible through the core area of the topsheet. In at least one embodiment, the printed pattern is printed on the backsheet. In at least one embodiment, the embossed pattern is substantially entirely embossed within the core area of the topsheet. In at least one embodiment, the printed pattern includes several at least partially visible occurrences of the printed decorative element and the embossed pattern includes several at least partially visible occurrences of the embossed decorative element. In at least one embodiment, the surface of the core area represents about 20% to about 80% of the surface of the topsheet. In at least one embodiment, the article has a thickness of less than about 5 mm.

BRIEF DESCRIPTION OF THE DRAWINGS

While the specification concludes with claims which particularly point out and distinctly claim the invention, it is believed the present invention will be better understood from the following description of preferred embodiments taken in conjunction with the accompanying drawings, in which like reference numerals identify identical elements and in which:

FIG. 4 is a top view of the body-facing side of another embodiment of the present invention;

FIG. 5 is a top view of the body-facing side of another embodiment of the present invention;

FIG. 6 is a top view of the body-facing side of another embodiment of the present invention;

FIG. 7 is a top view of the body-facing side of another embodiment of the present invention.

FIG. 8 is a top view of the body-facing side of another embodiment of the present invention.

FIG. 9 is a top view of the backsheet of FIG. 8.

DETAILED DESCRIPTION OF THE INVENTION

While the specification concludes with claims which particularly point out and distinctly claim the invention, it is believed the present invention will be better understood from the following description.

DEFINITIONS

Unless explicitly stated otherwise, the term "comprising" is to be construed as open ended, meaning that other features, steps or ingredients can be added as long as they are suitable to be used in a feminine absorbent hygiene article. The article "a" is to be construed as "one or more" unless specifically otherwise indicated. Thus for example "a decorative element" means "one or more decorative elements".

As used herein, the term "feminine hygiene articles" refers to the type of absorbent articles worn externally by women, usually to absorb vaginal discharge and/or urine leak. The term feminine hygiene articles include such articles commonly referred to as pads, pantiliners, liners, sanitary napkins, sanitary towels, or interlabial devices. These articles are typically held in place adjacent the user's pubic region by the user's undergarment, and may be affixed thereto via adhesive or other joining means.

As used herein, the term "pattern" generally refers to any shapes, forms, graphics, symbols and combinations thereof. Examples of pattern can be purely abstract geometric shapes, such as circles or waves, and/or be evocative of natural elements such as floral patterns, and/or be evocative of certain texture or fabrics such as laces. The embossed and printed patterns of the invention can normally be visually recognizable. Embossed patterns may also be recognizable by touch.

Absorbent Article 10

Figure 1:
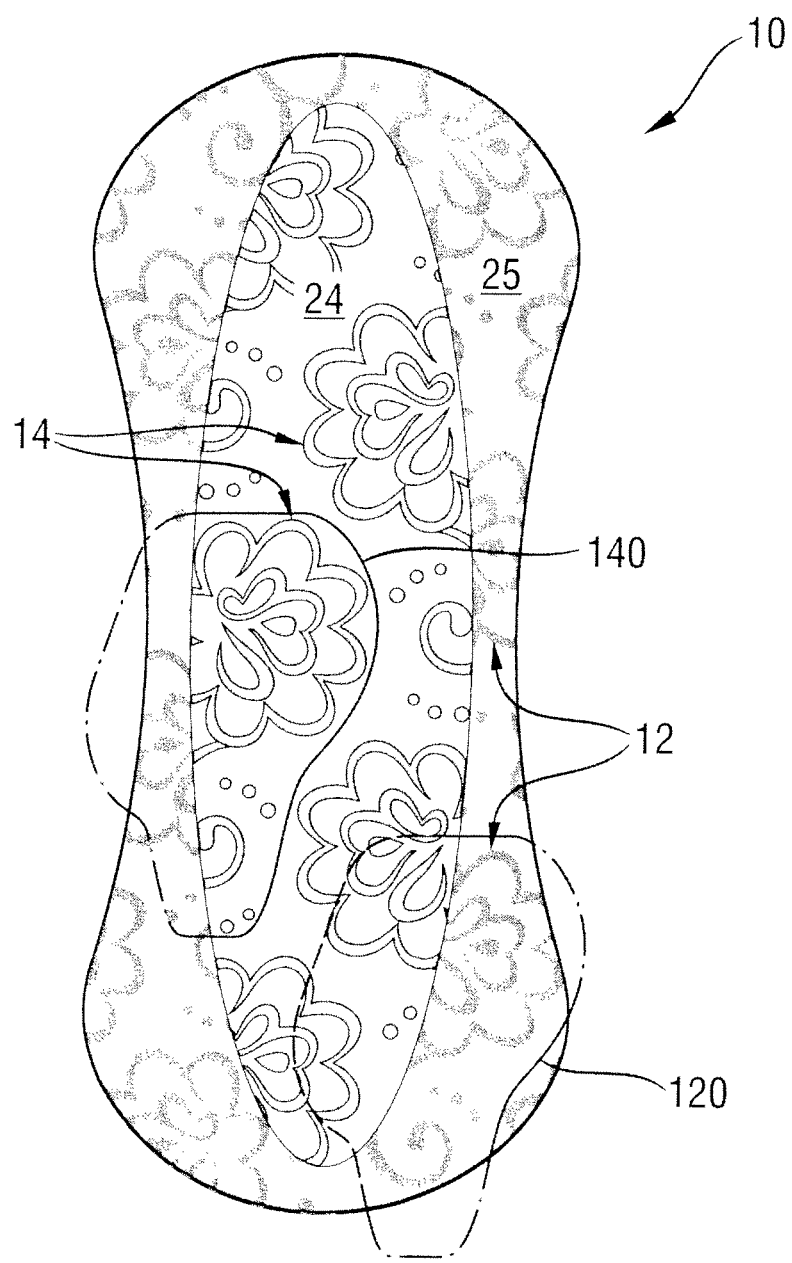
FIG. 1 is a top view of the body-facing side of an embodiment of the present invention.

FIG. 1 shows a top view of the body-facing surface of an exemplary feminine hygiene article 10 according to the invention. The particular embodiment shown is an example of a pantiliner (also sometimes designated as a "liner" or "pantyliner"), but the present invention is not limited thereby. Feminine hygiene articles normally have a generally flat body-facing surface but are generally flexible to adapt to the user's anatomy and movements. They can also be folded, for example, to reduce the size of the packaging before use. The articles of the invention comprise a printed pattern 12 and an embossed pattern 14.

Figure 2:
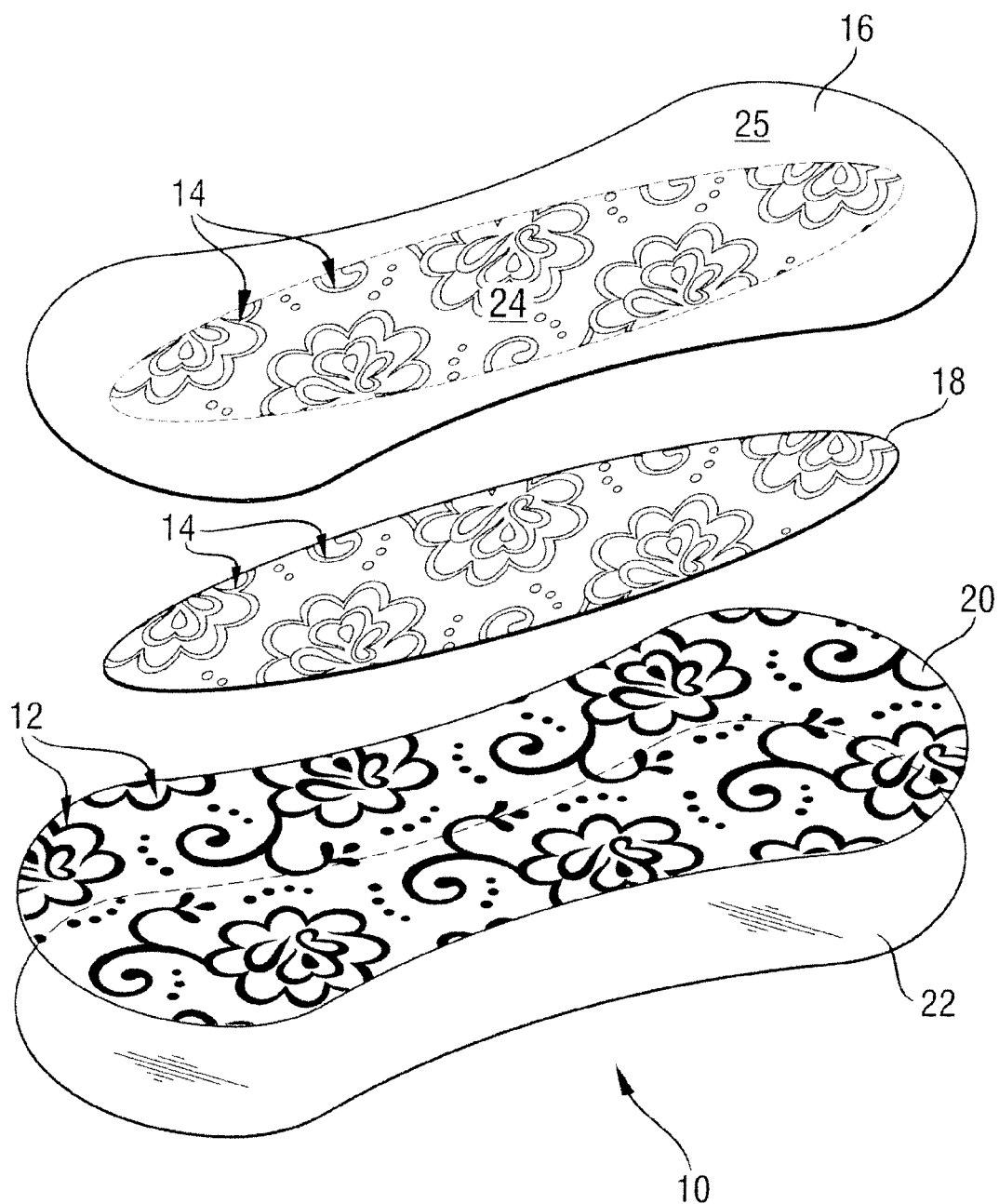
FIG. 2 is an exploded view of the article of FIG. 1 showing the different layer constituting the exemplary embodiment of FIG. 1.

FIG. 2 represents the article of FIG. 1 in an exploded view showing, from top to bottom, the following layers: a topsheet 16 having a core area 24, an absorbent core 18, and a backsheet 20. A releasable cover 22 which may be used to cover an adhesive material on the outer-surface of the backsheet 20 is also represented. The "top" of article is defined herein as the surface of the article oriented toward the user's body, and the "bottom" is defined herein as the opposite surface of the article, i.e. the surface that will generally contact the woman's undergarment. As used herein, the term "core area" refers to the area 24 of the topsheet (i.e. the body-facing side of the article) directly overlying the absorbent core 18.

As shown in FIG. 2, the printed pattern 12 may be printed on a layer placed below the core 18, thus avoiding direct contact of the ink with the user's skin. The layer on which the printed pattern 12 is printed may be the backsheet 20 itself, as shown in the Figures, or another layer, if present. The embossed pattern 14 may be embossed on the topsheet and/or the core, if present, as represented in the Figures.

A releasable cover 22 is normally present in feminine hygiene articles. The releasable cover may protect the adhesive that may be present on the outside side of the backsheet before use. The releasable cover is normally discarded by the user when the absorbent product 10 is placed in the undergarment. Although the releasable cover may be printed if present, it is not considered as a printed layer comprising a printed pattern in the sense of the invention since it is discarded at the point of use. Similarly, when referring to the thickness of the article herein, the thickness of the releasable cover 22 is not taken into account.

Printed Pattern 12

The feminine hygiene articles of the invention comprise a printed pattern 12 that may be printed on any layers of the articles. It may, however, be desirable to print the printed pattern 12 on a layer which is not the topsheet to avoid contact of the printed layer with the skin of the user. Thus, contact of the dye or ink used to print the printed pattern 12 with the user's skin may be avoided. This may be desirable because some users have an apprehension that any ink or dye used may present a health risk, such as an allergy. Another advantage is that when a lotion is used on the topsheet, for example, to provide a better feel, any possible "bleeding" of the printed pattern 12 that the lotion may cause may be limited.

The printed pattern 12 may be in particular printed on one of the layers situated below the absorbent core 18, if an absorbent core is present. In the embodiments represented in the Figures, the printed pattern 12 is printed on the otherwise generally white backsheet 20 of the article, but it is not excluded that another layer below the core 18 may be printed as well or instead. For example, the printed pattern 12 may be disposed on an optional secondary backsheet, if present.

The surface coverage of the printed pattern 12 on the printed layer may vary. It may however be desirable to have a printed surface coverage ranging from about 2% to about 40% of the total surface of the printed layer. Below about 2%, the printed area may not be large enough. Above about 40% surface coverage, the increased costs due to the increased amount of ink and increased drying time used may be disadvantageous. Accordingly, a surface coverage of between about 8% and about 25% may be desirable, providing a good cost-benefits balance.

The printed pattern 12 may be printed with any conventional printing method, such as flexo print or roto gravure printing. The printed pattern 12 may be advantageously printed with an ink sufficiently colored to be visible through at least a portion 25 of the topsheet 16 of the article 10 outside the core area 24. Any colored ink may be used, including, but not limited to black or colors such as, for example, pink, violet, green, purple, blue, yellow, gold, silver, etc., or any combination of different colors. In addition to printed patterns obtained by conventional printing, the term "printed pattern" encompasses patterns obtained by techniques that may not typically be referred to as printing, but that provide the same or a similar effect. For example, it may be possible to provide a similar visual effect by heat crimping a plastic nonwoven layer (e.g. backsheet) so that the crimped area, which then becomes translucent, provides a similar visual effect as an ink printed area. For example, if the panty of the user is colored, the color of panty will be more visible through the crimped zone.

In conventional absorbent articles, the topsheet, and more generally all the layers except the absorbent core, are to some extent transparent or translucent. Thus, even if the printed pattern is printed on a layer which is not the topsheet, the printed pattern may still be visible through at least the area 25 of the topsheet outside the core area 24 when using an ink of even relatively low intensity. Even if a secondary topsheet is present, such a layer is also normally at least partially translucent. By "visible", we mean that a subject having a good vision in both eyes (10/10) holding the article at a distance of about 50 cm in a brightly lit room with incandescent light can see the printed pattern. On the other hand, most conventional core materials are opaque, so that the printed pattern 12 is normally not visible through the core area 24 when the printed pattern 12 is printed on a layer 20 situated below the core 18. The printed pattern 12 is in that case however normally visible through the area 25 of the topsheet 16 which is outside the core area 24 of the topsheet 16.

Although not required by the invention, an ink with hydrophobic character may be desirable to prevent the ink from "drawing" fluids away from the core. Many commercial inks are solvent-based and therefore capable of providing a hydrophobic effect. In addition, hydrophobic agents such as oils or waxes may be added to the commercial ink composition if desired. A "solvent-based" ink does not use water as the mobile phase to carry various pigments, resin(s) or binder(s), and additives, such as wax. Typically, "solvent-based" inks use one or more of various organic solvents such as alcohols, esters, aliphatics, and aromatics to solubilize these components. Solvents that solubilize resins well are generally referred to as "active", while those that are not "active" are called "diluents. Solvent-based inks that typically use aliphatic hydrocarbons with common binder types, such as polyamide, shellac, rosin esters, nitro-cellulose, and styrene maleic are suitable for use herein. Examples of suitable inks are supplied by Sunchemical/Hartmann Niederhausen/TS under the trade name P-3228/811 PMS 270 Lavender or trade name V8185/811 PMS 382 Green. A "water-based" ink typically uses water predominantly as the mobile phase. Water-based inks may also be suitable for the invention if they do not substantially negative impact on the product's performance.

Embossed Pattern 14

The articles of the invention comprise an embossed pattern 14, which may be disposed on the topsheet 16 of the article 10. As shown in the Figures, the embossed pattern 14 may be substantially entirely encompassed within the core area 24 of the topsheet immediately situated above the absorbent core 18, if present. The core 18, if present, may also be at least partially embossed by the embossed pattern 14. In a conventional embossing process, it is usual that topsheet and absorbent core are embossed together in a single step, but it is not required. The invention does not necessarily require the presence of a core 18 because some topsheet layers, such as an air through carded topsheet or other layers, may be sufficiently thick to provided with a visible embossment. However, it may be desirable within the present invention to have an absorbent core situated between the topsheet and backsheet, to increase the absorbency capacity of the article and/or to facilitate the embossing of the embossed pattern. Embossing may also be present in the area of the topsheet 25 outside the core are 24.

The embossing can be achieved with standard techniques such as thermal bond, ultrasonic bond and/or pressure. An example of a suitable process is thermal bonding wherein the layers are passed through two steel rolls where one is engraved with the visual pattern and the other is flat. In certain embodiments, one or both of the rolls are warmed to temperature suitable to at least partially melt one or more layer (typical range from 90 to 170° C.).

The embossing roll may be engraved using conventional techniques such machine tooling for most embossing patterns, but it may be desirable to use acid etching or laser engraving to provide a finer engraving, and thus a finer embossed pattern. It may be desirable that the embossed pattern comprises relatively thin embossing features, much thinner than the embossed channels previously disclosed in the art, such as in WO2004/006818. Thin embossing features may provide a generally feminine and delicate look to the article. The embossing tool should therefore capable of high definition embossing, in particular with a resolution (minimum thickness of the embossed lines) of less than about 0.75 mm, in particular but not limited to between about 0.35 mm and about 0.60 mm. Similarly, the resolution of the printed pattern (corresponding to the minimum thickness of a printed line) may be of less than about 0.75 mm, in particular but not limited to between about 0.35 mm and about 0.60 mm.

Printed Decorative Element 120 and Embossed Decorative Element 140

The printed embossed pattern 12 of the invention comprises at least one embossed decorative element 120. By "decorative element" we mean an element of the embossed pattern 12 whose main function is to provide an aesthetic feature to the article, although the decorative element may also have a functional benefit other than purely aesthetic. For example, the embossed pattern 14 may also generally provide improved fluid acquisition or bonding between the layers. However, where the embossments have a sole or primarily a functional role, such as the embossed channels disclosed in WO2004/006818, such embossments are not considered decorative elements in the sense of the present application. In general, the printed pattern 14 has no other function than being decorative, so that the printed pattern will normally always comprise a printed decorative element 140, be it the printed pattern itself.

It has been found that having an embossed pattern comprising a embossed decorative element and a printed pattern may provide the article with an improved overall appearance, in particular when the printed pattern comprises a printed decorative element which is substantially similar to the embossed decorative element. By "substantially similar", it is meant that the printed decorative element 120 and the embossed decorative elements 140 have substantially the same design and have substantially the same size. By "substantially the same design", it is meant that the design of the printed decorative element and the design of the embossed decorative element are substantially the same, although the way the outline of the designs is marked may differ between the embossed decorative element and the printed decorative element. For example the printed decorative element may be printed as a continuous line, whereas the embossed common decorative element may be embossed as a dotted line or a broken line or maybe thicker or thinner than the printed decorative element, and vice versa. Decorative elements orientated in different directions or mirror-images of each other are also considered to have substantially the same design. By "substantially the same size", it is meant that the size ratio between the printed decorative element and the embossed decorative element may range from about 25% to about 400%, including a ratio of from about 50% to about 200%.

FIGS. 1 to 7 show examples where the printed pattern 12 and the embossed pattern 14 comprise as decorative elements a floral or more generally a vegetal decorative element 120, 140. In FIG. 1 for example, the printed decorative element 120 and the embossed decorative element 140 comprises a stylized flower.

As previously mentioned, there is often a dislike by users to have a printed pattern on a layer of the article directly in contact with the skin, which is normally the topsheet 16. Although printing a printed pattern 12 on the backsheet 20 or another layer below the core 18 is a solution to the problem of avoiding direct or close contact between the printed pattern 12 and the skin of the user, the absorbent core 18 is often opaque and the printed pattern 12 is then only visible through the area 25 of the topsheet 16 outside the core area 24. This leaves the relatively large core area 24 of the topsheet 16 without visible ornamentation. The inventors have found that it was possible to provide an improved appearance of the whole of the body-facing side of the article by providing the topsheet 16, in particular within the core area 24, with an embossed pattern 14 having a decorative element 120. In particular, the embossed decorative element may be substantially similar to the decorative element 140 of the printed pattern 14. An improved appearance may also be achieved in other configurations. For example notwithstanding the above, it is possible to partially or completely print the topsheet with the printed pattern along the longitudinal sides of the topsheet, the embossed pattern being present in the core area to still provide an article with an improved appearance coming from the combination of the printed pattern and the embossed pattern, in particular if those patterns have substantially similar decorative elements.

When an absorbent core is present, the embossed pattern 14 may improve the appearance of the core area 24 of the topsheet, without the need for printing the topsheet 16 on its core area 24. The appearance of the area 25 of the topsheet outside the core area 24 may then be improved by the printed pattern which is visible by transparency through the topsheet if it is printed on a layer below the core. When the printed pattern and embossed pattern comprise decorative elements that are substantially similar, a further advantage is that a seamless or unitary impression may be provided on the topsheet between the core area 24 and the area of the topsheet 25 outside the core area 24, without the need to print across the whole topsheet.

The printed pattern 12 and the embossed pattern 14 may or may not be registered. However, in practice, it may be difficult and/or costly to register both patterns due to the constraints of modern high speed production and the general desire to avoid scrap. Thus, the printed pattern and embossed pattern may be chosen such that in a non-registered configuration, they still provides the benefit of the invention (e.g. as shown in FIG. 1).

The printed decorative element 120 may appear in multiple occurrences within the printed pattern 12. The embossed decorative element 140 may appear in multiple occurrences within the printed pattern 14. In this case, a "wallpaper" arrangement of the decorative elements in any or both of the printed pattern 12 and the embossed pattern 14 may be used. The decorative elements may also be orientated in different direction or mirror image of each other within the respective patterns.

As shown, for example, in FIG. 1, the printed decorative element 120 and the embossed decorative element 140 may not be entirely visible for each, or even any, of their multiple occurrences. For example, with an oval shaped core as represented, it is normal that in the narrowing region of the core area there may be occurrences of the embossed decorative element that are truncated. Similarly, some or all printed decorative elements may be to some extent truncated by the way the printed layer is cut or, if present, the absorbent core is placed.

The embodiment of FIG. 4 provides an example wherein the printed decorative elements 120 are somewhat larger than the embossed decorative elements 140, while still being substantially similar and providing an improved and integrated appearance to the body-facing surface of the product.

The printed pattern 12 and embossed pattern 14 shown in the embodiment of FIG. 5 comprise vegetal inspired decorative elements 120, 140. As represented in FIG. 5, the embossed pattern 14 and/or the printed pattern 12 may each comprise further decorative elements that are not substantially similar with any of the decorative elements present in the other pattern. For example, the printed pattern 12 on FIG. 5 also comprises a net-like decorative element 26 in addition to the floral printed decorative element 120. It is not believed to be detrimental for the improved appearance of the article to have further non-common decorative elements in the printed pattern and/or embossed pattern. However, if the printed and embossed patterns comprise printed decorative element and embossed decorative element that are substantially similar, it may be desirable to keep the substantially similar decorative elements clearly visible within the printed pattern and embossed pattern.

FIG. 6 shows an example of an embodiment of the present invention wherein the printed decorative element 120 is printed in continuous lines, whereas the embossed decorative element 140 is embossed as series of dots. The embossed decorative elements formed by the dots however provide substantially the same design as the printed decorative elements.

FIG. 7 shows an embodiment wherein the printed and embossed decorative elements 120, 140 are also of floral inspiration. The embossed floral decorative element in the embossed pattern 14 is represented partly in continuous and partly in dotted lines.

FIG. 8 represents an embodiment where the common decorative element 120, 140 is not a floral element, but is formed by the combination of finely embossed and printed dots and dashes, which may be for example evocative of traditional laces, and are printed and embossed to respectively form the printed pattern 12 and the embossed pattern 14. The backsheet 20 as a printed layer is shown on isolation on FIG. 9.

Lace Effect

The vegetal and floral decorative elements of the printed patterns and embossed patterns shown in FIG. 1-7 and the non-vegetal decorative elements shown in FIG. 8 were also found to be to provide the appearance, or at least provide the impression of appearance to the user of lace fabric to the articles on which they were applied. Lace fabrics have been traditionally used in women's underwear. The printed and embossed patterns used may, at least partially, reproduce some of the design elements traditionally found in lace fabrics, such as floral elements as exemplified in FIG. 1-7 and/or the fine, discrete elements as exemplary shown on FIG. 8. Another factor for providing the article with the appearance of lace is using high definition embossing and printing, as indicated above. It may be desirable that a resolution of less than about 0.75 mm, for example between about 0.35 mm and about 0.60 mm, is reached on at least a portion of both printed and embossed patterns. With high resolution printing and embossing, thin lines or other features having a thickness within the resolution range may be printed or embossed, thus helping to provide an appearance of fine lace fabric to the article. Thicker lines (or other features) may also be present within the printed pattern and the embossed pattern.

Backsheet 20

Any conventional backsheet materials suitable for printing, such as polyolefinic films or nonwoven webs, may be used as backsheet. In some embodiments, the backsheet may be impervious to malodorous gases generated by absorbed bodily discharges, so that the malodors do not escape. The backsheet may or may not be breathable. A low density polyethylene backsheet about 0.01 to about 0.08 millimeters in thickness, is an example of a suitable backsheet material. A polyethylene film, such as is sold by the Tredegar Corporation of Terre Haute, Ind., under model X-813 may also be used. Further, the backsheet may be made of a soft cloth like material which is hydrophobic relative to the topsheet, e.g. a polyester or polyolefinic fiber backsheet.

Figure 3:
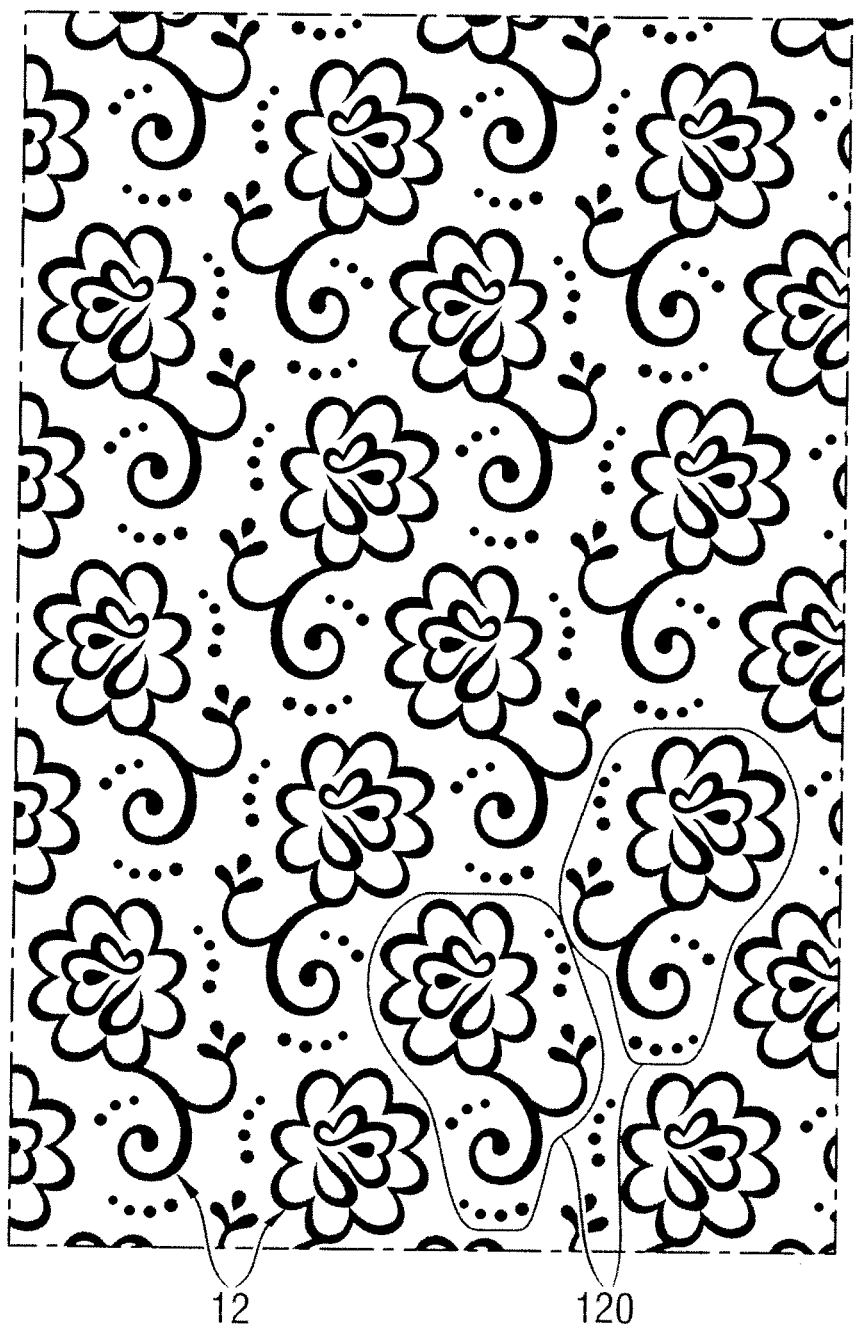
FIG. 3 is a view of a nonwoven material with a printed pattern comprising several decorative elements in a wallpaper configuration, prior to being formed into a backsheet according to the invention.

FIG. 3 represents is a view of a nonwoven material printed with a "wall-paper" pattern of floral elements prior to being formed into a backsheet according to the invention. FIG. 9 shows the backsheet layer of the embodiment of FIG. 8 in an isolated view.

The printed pattern 12 may be printed on any side of the printed layer, but if the printed layer is the backsheet, it may be beneficial to print the layer on the "top", i.e. the body-facing side, of the backsheet layer, although this is no required.

Topsheet 16

Any conventional topsheet materials may be used within the invention. Suitable topsheets may be made from nonwoven materials or apertured polyolefinic films. If desired, the topsheet may include a surfactant to enhance liquid penetration to the core. The topsheet and in particular the central fluid acquisition zone, may be hydrophilic. A surfactant density of about 0.01 milligrams per square centimeter of topsheet area is normally suitable. A suitable surfactant is sold by the Glyco Chemical, Inc. of Greenwich, Conn. as Pegosperse 200 mL.

The topsheet may have a plurality of apertures to permit liquids deposited thereon to pass through to the core. An apertured polyolefinic film topsheet having about 5 percent to about 50 percent open area, typically about 25 percent open area, and a thickness of about 0.01 millimeters to about 0.05 millimeters prior to aperturing and about 0.42 millimeters to about 0.51 millimeters after aperturing is usual.

One exemplary suitable apertured topsheet for use herein are nonwoven topsheet. Suitable nonwoven materials/layers include fibrous nonwoven materials/layers formed by a carding process or a spunbond process or meltblown process whereby molten polymeric material is extruded through a die, attenuated to lengthen the extruded polymer into fibres and decrease the diameter thereof and is subsequently deposited on a forming surface. Polymeric materials suitable for use in forming such fibrous nonwoven materials/layers include polyolefins such as polyethylene and polypropylene, polyesters, nylons, ethylene vinyl acetate, ethylene methacrylate, copolymers of the above materials, block copolymers such as A-B-A block copolymers of styrene and butadiene, and the like.

Absorbent Core 18

It may be desirable that the article comprises an absorbent core 18 disposed between the topsheet 16 and the backsheet 20. As used herein, the term "absorbent core" refers to a material or combination of materials suitable for absorbing, distributing, and storing fluids such as urine, blood, menses, and other body exudates. Because typical absorbent cores used in feminine hygiene articles are relatively thick and bulky compared to the other layers, they often may be easier to emboss than other layers of the article.

The size and shape of the absorbent core 18 may be such that the core area 24 has a substantially smaller surface than the topsheet 16 of the article. By "substantially smaller", we mean that the surface of the core area 24 is at least about 10% smaller than the overall surface of the topsheet 16. The ratio of the surface of the core area 24 to the overall surface of the topsheet 16 may desirably be comprised within any of the following ranges: between about 15% and about 90%, between about 30% and about 70%, between about 40% and about 60%. An oval shaped core may easily provide this ratio with an article having a generally rectangular or "dog-bone" shaped outline, as represented in the Figures. By providing an absorbent core with a smaller surface than the topsheet, several benefits are achieved. First, the amount of material used is reduced, reducing the overall costs of manufacturing the product. Second, a core having a smaller surface may increase the overall flexibility of the product, because the sections of the product not provided with a core are generally less rigid than the region where the core is situated.

The absorbent core 18, when present, may be generally centered in the middle of the article, and may be disposed away from the periphery of the article to provide improved flexibility along the edges of the article.

The core represented in the drawings has an oval shape, but the shape of the core may of course be any suitable shape, for example hour-glass shaped. It is also typical for absorbent cores to be rectangularly shaped for ease of manufacturing. However, flexibility may be better with cores having a curved shape and not comprising right angles.

The absorbent core of the invention can be made of any suitable liquid-absorbent material. Non-limiting examples of liquid-absorbent materials suitable for use as the absorbent core include comminuted wood pulp which is generally referred to as airfelt; creped cellulose wadding; absorbent gelling materials including superabsorbent polymers such as hydrogel-forming polymeric gelling agents; chemically stiffened, modified, or cross-linked cellulose fibers; meltblown polymers including co-form; synthetic fibers including crimped polyester fibers; tissue including tissue wraps and tissue laminates; capillary channel fibers; absorbent foams; absorbent sponges; synthetic staple fibers; peat moss; or any equivalent material; or combinations thereof.

If the absorbent article is designed to be used as a pantiliner, the thickness of the core may be relatively low, in particular compared to thicker absorbent articles such as "thick" sanitary napkin or even the so called "Ultra" sanitary napkin that normally have a thickness above 5 mm. Thus, it may be desired that the absorbent core comprise superabsorbent polymer (SAP), normally distributed within a matrix of cellulosic fibers.

The absorbent core may be unitary, or may be a laminate of two or more layers. For example, the core may comprise a fluid impermeable barrier layer (e.g. a PE Patch) on its backsheet-facing side to prevent fluids retained by the absorbent core from striking through the pantiliner and soiling adjacent garments. An exemplary PE patch is a 25 gsm poly film available form Britton Taco (UK) under trade name ST-012A-White.

Further generic information regarding absorbent cores can be found in prior patent publications, for example WO0207662A1 and WO9119471.

Secondary Topsheet

The articles of the invention may optionally include a secondary topsheet layer intermediate the topsheet 16 and the absorbent core 18. Such a secondary layer may be manufactured from a wide range of materials such as woven, nonwoven materials, polymeric materials such as apertured formed thermoplastic films, apertured plastic film, hydro formed thermoplastic films, porous foams, reticulated foams, reticulated thermoplastic films and thermoplastic scrims. Any material described herein before for the topsheet can be used for the secondary layer. In certain embodiments, this secondary topsheet layer underlies the topsheet on the entire surface thereof, i.e., the secondary layer extends to the periphery of the topsheet so that the secondary layer underlies the topsheet on the entire inner surface of the topsheet.

The purpose of the secondary topsheet is normally to readily transfer the acquired body fluid from the topsheet to the absorbent core, the transfer of fluid occurring not only vertically in the thickness of the secondary topsheet, but also along the length and the width directions of the absorbent product. This helps the fluid capacity of the underlying storage layer to be fully utilized.

Secondary Backsheet

The articles of the invention may optionally include a secondary backsheet layer intermediate the absorbent core 18 and the backsheet layer 20. The purpose of the secondary backsheet is generally to retard or prevent liquid from passing from the absorbent core to the outside of the product, while allowing free air flow through it. An example of secondary backsheet is a resilient three dimensional polymeric web, which consist of a liquid impervious film which has apertures forming capillarity or cones. The film with capillaries or cones may be oriented such that the apexes of the cones face the absorbent core to prevent passage of fluid. The capillaries or cones can have a slanted shape in order to partly close or completely close when compressed.

Adhesive Means

The outwardly oriented face of the backsheet 20 may comprise means for attaching the sanitary napkin to the undergarment of the wearer. Pressure sensitive adhesives have been commonly found to work well for this purpose. The adhesive may be continuous or intermittent. For example, the adhesive may be applied in strips or across the entire surface of the backsheet. The adhesive may be applied via any suitable method, including, but not limited to direct slot coating. A so called "finger lift", such a small area of the backsheet where no adhesive are applied and where the release cover is not attached to the backsheet, may also be provided to ease the removal of the releasable cover by the user.

Release Cover 22

The backsheet surface is normally entirely or partially coated by the adhesive means and is therefore typically provided with a release cover to avoid contamination of the adhesive means prior to use. The release cover is generally intended to be removed at the point of use. The releasable cover may be a silicone coated release paper, a plastic film or any other easily removable cover. The releasable cover may be in a single piece or in a multitude of pieces, e.g. to cover the individual adhesive areas. It also can perform other functions such as providing individualized packaging for the article or provide a disposal function. Any commercially available release paper or film may be used. Suitable examples include BL 30 MG-A SILOX EI/O, BL 30 MG-A SILOX 4 P/O available from Akrosil Corporation, and M&W films available from Gronau in Germany, under the code X-5432.

General

The articles of the present invention may have any suitable shape and/or dimensions. For example, the length of such products will normally lie in a range of from about 8 cm to about 20 cm, and the width may be from about 3 cm to about 9 cm width. The overall surface of the article (typically the surface of the backsheet and the topsheet) may also lie within the usual range found for these articles, which normally would be of from about 40 cm$^2$ to about 250 cm$^2$. For the purpose of providing exemplary dimensions of a pantiliner such as the one represented in the Figures, such a pantiliner may have a length of about 15 cm, a width (at center) of about 4.8 cm, an overall surface of the article of about 79 cm$^2$ and a core area surface of 38 cm$^2$. An exemplary thickness of the article represented is about 0.9 mm.

The thickness (also called "caliper") of the absorbent articles according to the invention may be less than about 5 millimeters, i.e. of a thickness relatively small compared to mainline feminine absorbent articles such as sanitary napkins as measured using the standard test described below. Desirably, the articles may be even thinner, to provide very discrete articles. The lowest limit for the thickness of the article will be dictated by technical feasibility. Typical articles have a thickness in the range of about 0.4 mm to about 3 mm, or from about 0.6 mm to about 2 mm. As used herein, the term "thickness of the article" refers to the thickness value measured approximately in the center of the article, i.e. normally taking into account the thickness of the core if present.

The article may or may not comprise so-called "wings", which are side-wrapping elements destined to be folded around the undergarment. These wings are often used for sanitary pads and are not normally present in products designated as pantiliners.

The articles of the invention are normally disposable, i.e. are not intended to be re-usable or washable after use.

Method of Manufacture

The sanitary articles of the present invention may be produced industrially by any suitable means. The different layers may thus be assembled using standard means such as embossing (e.g. thermal bonding) or gluing or combination of both. The converting line may comprise a printed step wherein the ink is applied to the printed layer of the article. It may, however, by simpler to carry the printed step on the printed layer outside the converting line of the article, before this layer is joined with any of the other layers.

Thickness Measurement

In one embodiment, the articles of the invention may be of the pantiliner type and be relatively thin and not bulky. For such articles, the thickness measurements will be less dependent of the pressure applied when making the measurement, than for example for bulky articles such as thick pads. However, in order to achieve reproducibility, the following method may be used to measure the thickness of the article of the invention. The equipment may comprise an apparatus capable of measuring thickness with a 0.01 mm tolerance. A commercial supplier of such equipment is for example Ono Sokki (www.onosokki.net), for example their Caliper Gauge GS-503 and digital readout DG 2610 may be used. The caliper gauge is fitted with a foot, which may have an exemplary 24.13 mm diameter. A suitable pressure exerted when the measurement is made is 0.689 kPa.

The test procedure is as follows. Make sure the micrometer is zeroed. Place the article without the release cover on the base plate, the topsheet facing up. If the article was provided in a compressed state (as is sometimes the case in certain packaging), the article is let to rest about 10 minutes before its thickness is measured. Similarly, if the article was provided folded, the article is first opened and let about 10 minutes to rest in its "flat" shape. Position the article on the base plate so that when the foot is lowered, it is in the center of the article. Let the foot gently lowers itself onto the article at a rate of 5 mm/sec+/−2 mm/sec. Determine the article caliper by reading the micrometer dial 10 seconds after the foot comes to rest. The shaft and foot should deliver approximately 32 grams of force for a pressure of 0.69+/−0.02 kPa to the sample with the above mentioned foot having a diameter of 24.13 mm.

Numerical Values

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

What is claimed is:

1. A feminine hygiene article comprising:
   i) a topsheet comprising a surface;
   ii) a backsheet joined to the topsheet;
   iii) an absorbent core placed between the topsheet and the backsheet, wherein the absorbent core defines a core area on the surface of the topsheet, and wherein a surface of the core area represents between 20% and 80% of the surface of the topsheet;
   iv) an ink printed pattern; and
   v) an embossed pattern,
   wherein the printed pattern comprises at least one printed decorative element and the embossed pattern comprises at least one embossed decorative element, and wherein the printed decorative element and the embossed decorative element are substantially similar; and
   wherein the printed pattern is printed on a layer of the article situated below the absorbent core, wherein the topsheet overlies the printed pattern, and wherein at least a portion of the printed pattern is visible through the topsheet.

2. The article according to claim 1 wherein the core area overlies the printed pattern and the printed pattern is not visible through the core area on the surface of the topsheet.

3. The article according to claim 1, wherein the printed pattern is printed on the backsheet.

4. The article according to claim 1 wherein the topsheet includes a surface, the absorbent core defines a core area on the surface of the topsheet, and the embossed pattern is substantially entirely embossed within the core area on the surface of the topsheet.

5. The article according to claim 1 wherein the printed pattern comprises several at least partially visible occurrences of the printed decorative element and the embossed pattern comprises several at least partially visible occurrences of the embossed decorative element.

6. The article according to claim 1 wherein the article has a thickness of less than 5 mm.

7. The article according to claim 1 wherein the article is a pantiliner.

8. A feminine hygiene article comprising:
i) a topsheet including a surface;
ii) a backsheet joined to the topsheet; and
iii) an absorbent core situated between the topsheet and the backsheet, wherein the absorbent core defines a core area on the surface of the topsheet which is smaller than the surface of the topsheet; wherein a surface of the core area represents between 20% and 80% of the surface of the topsheet;
iv) an ink printed pattern which is printed on a layer of the article situated below the absorbent core, wherein at least a portion of the printed pattern is visible through at least a portion of an area of the topsheet which is outside the core area; and
v) an embossed pattern which is at least partially embossed within the core area and which comprises an embossed decorative element, wherein the printed pattern comprises a printed decorative element and wherein the printed decorative element and the embossed decorative element are substantially similar.

9. The article according to claim 8 wherein the topsheet overlies the printed pattern, and the printed pattern is not visible through the core area on the surface of the topsheet.

10. The article according to claim 8 wherein the article has a thickness of less than 5 mm.

11. The article according to claim 8, wherein the printed pattern is printed on the backsheet.

12. The article according to claim 8 wherein the embossed pattern is substantially entirely embossed within the core area of the surface of the topsheet.

* * * * *